(12) United States Patent
Ingenhoven et al.

(10) Patent No.: US 7,529,598 B2
(45) Date of Patent: May 5, 2009

(54) POSITIONING DEVICE AND METHOD

(75) Inventors: Nikolaus Ingenhoven, Uerikon (CH); Christian Strebel, Greifensee (CH); Peter Fisch, Hombrechtikon (CH); Joas Leemann, Ottikon (CH)

(73) Assignee: Tecan Trading AG, Maennedorf (CH)

( * ) Notice: Subject to any disclaimer, the term of this patent is extended or adjusted under 35 U.S.C. 154(b) by 1006 days.

(21) Appl. No.: 10/869,297

(22) Filed: Jun. 16, 2004

(65) Prior Publication Data

US 2004/0267405 A1 Dec. 30, 2004

(30) Foreign Application Priority Data

Jun. 20, 2003 (CH) .................................... 1080/03

(51) Int. Cl.
- *G06F 19/00* (2006.01)
- *E06H 2/00* (2006.01)
- *G01N 21/00* (2006.01)
- *G01N 35/00* (2006.01)
- *C12M 2/00* (2006.01)

(52) U.S. Cl. .................. 700/245; 414/277; 414/222.12; 414/274; 414/280; 414/800; 422/63; 422/64; 422/65; 422/67; 422/68.1; 436/43; 436/44; 435/288.3; 435/288.5; 435/305.1

(58) Field of Classification Search ................. 700/259; 219/125.1; 356/141.5; 414/744.2
See application file for complete search history.

(56) References Cited

U.S. PATENT DOCUMENTS

| | | | | |
|---|---|---|---|---|
| 4,613,803 A | * | 9/1986 | Hasegawa et al. ............. 701/23 |
| 4,892,993 A | * | 1/1990 | Stol ........................ 219/125.1 |
| 4,932,777 A | * | 6/1990 | Fodale et al. .............. 356/141.5 |
| 4,955,780 A | * | 9/1990 | Shimane et al. ........... 414/744.2 |
| 5,443,792 A | * | 8/1995 | Buhler ........................ 422/67 |
| 5,563,798 A | * | 10/1996 | Berken et al. ................ 700/218 |
| 5,905,850 A | * | 5/1999 | Kaveh ....................... 700/259 |
| 6,627,160 B2 | * | 9/2003 | Wanner ....................... 422/100 |
| 2003/0055533 A1 | * | 3/2003 | Bacchi et al. ................ 700/275 |
| 2003/0215365 A1 | * | 11/2003 | Sevigny et al. ................ 422/64 |

FOREIGN PATENT DOCUMENTS

| | | |
|---|---|---|
| DE | 2 338 985 | 8/1973 |
| DE | 19 754 857 | 7/1998 |
| DE | 199 23 222 | 5/1999 |
| DE | 102 30 772 | 7/2002 |
| EP | 0 555 739 B1 | 8/1993 |
| JP | 06170768 | 6/1994 |
| WO | WO 03/059580 | 7/2003 |

* cited by examiner

*Primary Examiner*—Dalena Tran
*Assistant Examiner*—Ian Jen
(74) *Attorney, Agent, or Firm*—Notaro & Michalos P.C.

(57) ABSTRACT

A plate and method for positioning functional elements in a system for working with fluid-containing samples includes a horizontal work field having a lengthwise dimension and a perpendicularly extending transverse dimension, as well as a robot arm with a functional element, aligned essentially perpendicularly to the work field in a Z direction. The robot arm can move the functional element in at least a partial region of the work field in the X and/or Y direction. The plate includes two light barriers which intersect inside the partial region, each having a transmitter and receiver whose scanning or detection beams each extend in a direction deviating from the X direction and/or from the Y direction.

21 Claims, 2 Drawing Sheets

POSITIONING DEVICE AND METHOD

RELATED PATENT APPLICATION DATA

This application claims priority of the Swiss Patent Application No. 1080/03 filed on Jun. 20, 2003.

FIELD OF THE INVENTION

The present invention relates to a device for positioning functional elements and/or containers in a system for working with fluid-containing samples according to the preamble of independent Claim 1, the system including an essentially horizontal work field having a lengthwise dimension X and a transverse dimension Y extending essentially perpendicularly thereto, and at least one robot arm having at least one functional element aligned essentially perpendicularly to the work field in a Z direction, the robot arm being able to move the functional element in at least a partial region of the work field in the X and/or Y and/or Z directions.

BACKGROUND OF THE INVENTION

Work platforms or systems for handling liquids, for example, pipetting liquids from containers and distributing liquids into the wells of a microplate, have devices according to the species so that the container and the robot arm may be placed in relation to one another in such a way that the liquid handling is executed automatically and reproducibly. It has been shown that the precision with which a pipette tip, for example, may be automatically positioned at a location on a commercially available work platform is insufficient to routinely and precisely approach the wells of a microplate having 1536 wells. Particularly if multiple pipettes positioned along a line are used, even the slightest twisting of the microplates positionable on at least a partial region of the work field in relation to the coordinate system of the robot arm become noticeable. These twists or deviations from the ideal position relate to values on the X, Y, and Z axes in the most unfavorable case. In the event of a too large error tolerance, the danger arises that one or more pipette tips, temperature sensors, and/or pH probes, or another oblong, thin object which is to be positioned in a well will be damaged by an impact on the wall of the well and/or the surface of the microplate. In addition, in the event of a hard impact of such an object with the microplate surface, the danger arises of sample loss, and contamination of the neighboring samples and the workspace. Precise approach to the well, in which no danger of unintended contact with parts of the microplate arises, is therefore a basic requirement for routine work with a liquid handling system which may be used for automatic assaying of blood samples, for example.

OBJECTS AND SUMMARY OF THE INVENTION

A first aspect of the object of the present invention is therefore to provide a device, using which the wells of a 1536-well microplate may be aligned to the coordinate system of the robot arm. A second aspect of this object relates to providing a device, using which the pipette tip or other oblong, thin objects may be aligned precisely on this robot arm.

This object is achieved in regard to the first aspect according to independent Claim 1 in that a device as described initially is improved by including two light barriers, each having a transmitter and a receiver, which intersect inside the partial region of the work field. In this case, the scanning or detection beams of the light barriers each extend in a direction deviating from the X direction and/or from the Y direction.

This object is achieved in regard to the second aspect according to Claim 9 in that a system having at least one device according to the present invention and a robot arm is suggested. In this case, the robot arm includes one single seat or multiple seats for functional elements and these seats include correction elements which are implemented to exert a force on each functional element and therefore to correct the position of each functional element in its seat in the X and/or Y and/or Z directions. Such systems according to the present invention are characterized in that these correction elements act on the functional elements in a direction which corresponds either to the extension direction of the detection beam of the first light barrier or to the extension direction of the detection beam of the second light barrier of the device according to the present invention. Additional preferred features of the present invention result from the dependent claims.

Objects or functional elements to be moved are generally implemented as oblong, thin, and extending in the Z direction, and may preferably also be raised and/or lowered in this direction. Typical functional elements are, for example, reference tips and/or reference needles for mutual adjustment and/or alignment of microplates and other vessels in relation to a coordinate system of a liquid handling system. Dispenser tips and pipette tips are also functional elements of this type, spray needles also being referred to as dispenser tips, for example. Fixed steel cannulas, disposable tips made of plastic, and "ZipTips™" (Millipore Corporation, 80 Ashby Road, Bedford, Mass. 01730-2271, USA), are referred to here as exemplary pipette tips. Electrodes, temperature sensors, pH probes, and optical fibers are also included in the preferred objects and/or functional elements to be positioned. In this case, microplates having, for example, 96, 384, or 1536 wells, but also troughs (e.g., for collecting waste or for providing a stock solution), test tubes having blood samples, for example, which are accommodated in a test tube holder, or other containers for samples or liquids are referred to as containers or vessels. "Carriers" are also identified as containers here. These are typically implemented for receiving three microplates and are used as a high-precision carrier for these microplates. Such carriers preferably have a pivot in one end region and have an adjustment screw for fine adjustment of the carrier surface in the X and/or Z directions in the other end region.

BRIEF DESCRIPTION OF THE DRAWINGS

In the following, the present invention will be described in greater detail on the basis of schematic figures of preferred embodiments, which do not restrict the scope of the present invention.

DETAILED DESCRIPTION OF THE INVENTION

Figure 1:
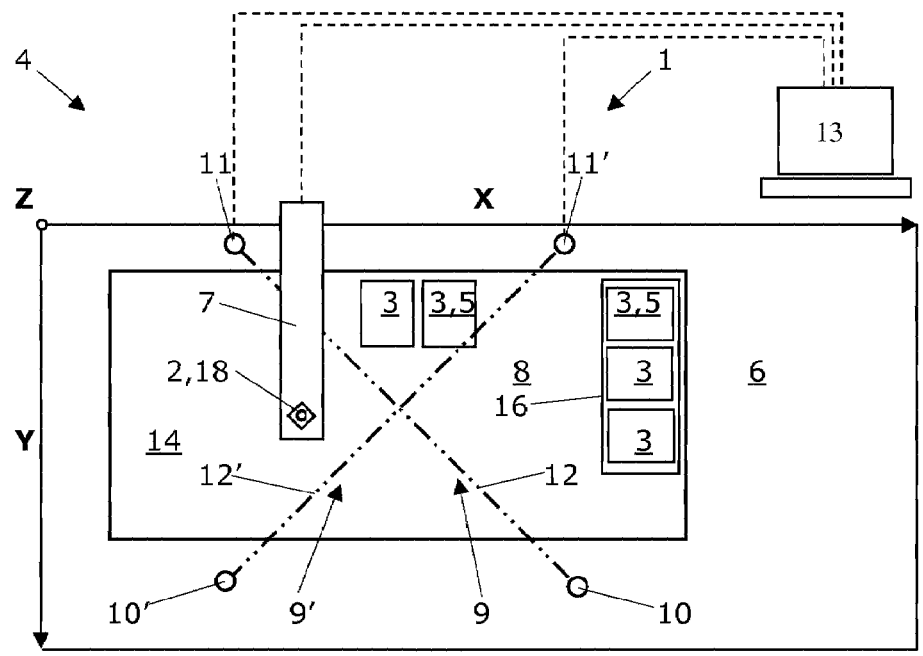
FIG. 1 shows a top view of a liquid handling system having a robot arm, which includes a single seat, an essentially horizontal work field, and a device for positioning functional elements and/or containers according to the present invention.

FIG. 1 shows a top view of a liquid handling system 4 having a robot arm 7, which includes a single seat 18, an essentially horizontal work field 6, and a device 1 according to the present invention for positioning functional elements 2 and/or containers 3. This system 4 for working with fluid-containing samples 5 includes an essentially horizontal work field 6 having a lengthwise dimension X and a transverse dimension Y extending essentially perpendicularly thereto. The robot arm 7 carries a functional element 2 aligned essentially perpendicularly to the work field 6 in a Z direction and may move this functional element 2 in at least a partial region 8 of the work field 6 in the X and/or Y and/or Z directions. The device 1 according to the present invention includes two light barriers 9, 9' intersecting inside the partial region 8 of the work field 6, each having a transmitter 10, 10' and a receiver 11, 11'. The detection beams 12, 12' of the light barriers each extend in a direction deviating from the X direction and/or from the Y direction.

Figure 3:
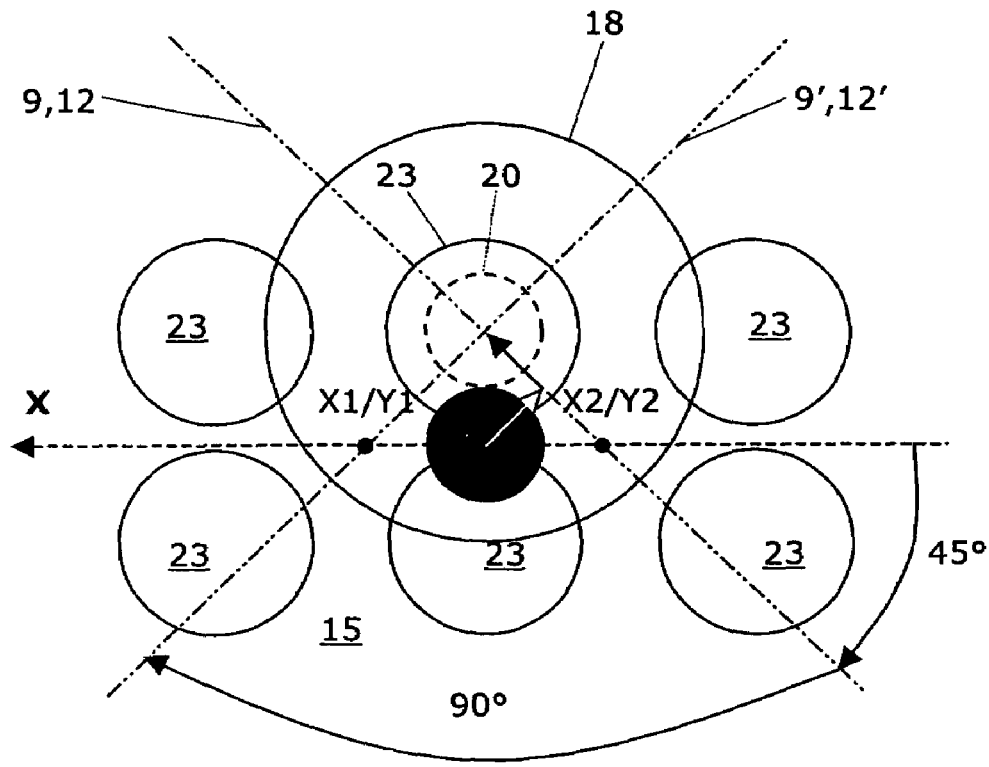
FIG. 3 shows a method scheme for determining the current position of a functional element to be positioned and for correcting this position.

The detection beams 12, 12' of the light barriers 9, 9' preferably intersect at an angle of essentially 90°, these detection beams extending at an angle of essentially 45° (cf. FIG. 3), both in relation to the X direction and in relation to the Y direction. In a preferred embodiment, the device includes a computer 13, which detects the movements of the robot arm 7 and/or the functional element 2 and analyzes the signals of the receivers 11, 11'. In this case, the computer 13 correlates these signals with the X/Y/Z position in the work field 6 of the functional element 2, which triggers these signals. The device may be integrated in a liquid handling system or include a plate 14 which has the external dimensions of a standard microplate 15. In the second case, the device 1 may be fixed on a high-precision carrier 16 for standard microplates, which is positioned inside the work field 6.

Figure 2A:
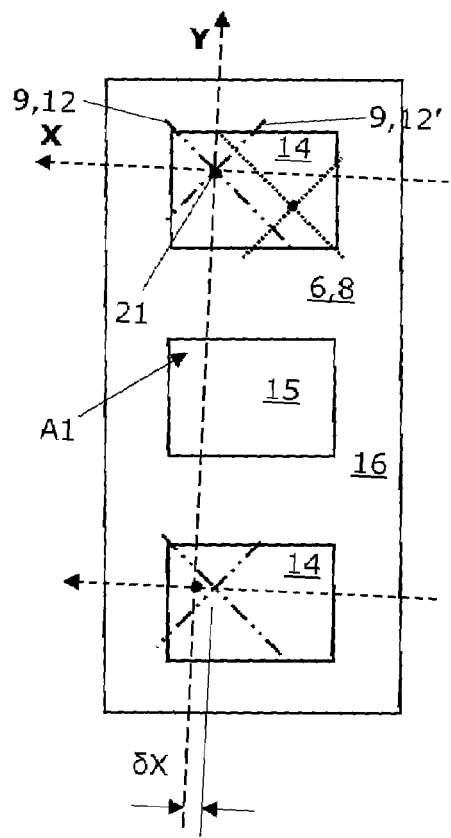
FIG. 2A showing a carrier twisted in relation to the coordinate system of the liquid handling system, and FIG. 2B showing a carrier aligned in relation to the coordinate system of the liquid handling system.
Figure 2B:
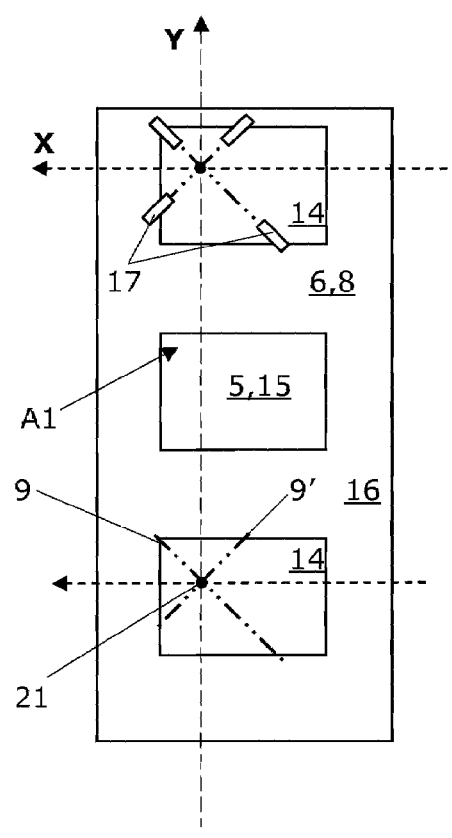
FIG. 2 shows a top view of a high-precision carrier for microplates.

FIG. 2 shows a top view of such a high-precision carrier 16 for microplates. In FIG. 2A, the carrier 16 is still twisted in relation to the coordinate system of the liquid handling system.

Before the alignment of the carrier, a plate 14 having a device 1 which has the external dimensions of a standard microplate 15 is fixed in a first position on a high-precision carrier 16 for standard microplates positioned inside the work field 6. The two light barriers 9, 9' are positioned on this plate 14, the detection beams 12, 12' of the light barriers 9, 9' intersecting in a point which is located in a defined position in relation to well A1 of a standard microplate 15.

In this way, because the intersection point is preferably located outside the middle of the plate, it becomes possible for an operator, by placing the plate 14, rotated by 180°, on the same place (the two light barriers are shown dotted in FIG. 2A), to check the alignment of the surface of the carrier along the X dimension of the work field 6 in the Z direction and correct it if necessary using adjustment screws.

Using the robot arm 7, a reference needle 21 is then positioned in the intersection point of the detection beams 12, 12' of the light barriers 9, 9', and the X, Y, and Z values of this first reference point are then stored in the computer 13. The movements of the robot arm 7 and/or of the functional element 2 are detected using a computer 13 which analyzes the signals of the receivers 11, 11' and correlates these signals with the X/Y/Z position in the work field 6 of the functional element 2, which triggers these signals.

The plate 14 having the device 1 is then fixed in a second position on the same high-precision carrier 16 for standard microplates 15 (cf. FIG. 2A, lower position). The robot arm 7 is positioned with the reference needle 21 in the theoretical intersection point of the detection beams 12, 12' of the light barriers 9, 9', where it is located at a distance of the absolute value of the error δX from the intersection point of the two light barriers. The high-precision carrier 16 is then moved in the X or Z direction until the reference needle 21 is located in the intersection point of the detection beams 12, 12' of the light barriers 9, 9' (cf. FIG. 2B). The carrier 16 is now aligned. If necessary, as already described, the alignment of the surface of the carrier along the X dimension of the work field 6 in the Z direction may be checked again and corrected using adjustment screws.

This method is used for positioning containers 3 in a system 4 for working with fluid-containing samples 5. In this case, the system 4 includes an essentially horizontal work field 6 having a lengthwise dimension X and a transverse dimension Y extending essentially perpendicularly thereto and at least one robot arm 7 having at least one functional element 2 aligned essentially perpendicularly to the work field 6 in a Z direction. The functional element 2 (a reference needle 21 here) is moved using the robot arm 7 in at least a partial region 8 of the work field 6 in the X and/or Y and/or Z directions. To perform this method, at least one device 1 is positioned in such a way that two light barriers 9, 9', each having a transmitter 10, 10' and receiver 11, 11', intersect inside the partial region 8 of the work field 6; the detection beams 12, 12' of the light barriers 9, 9' each extend in this case in a direction deviating from the X direction and/or from the Y direction. It is especially preferable if the detection beams 12, 12' of the light barriers 9, 9' intersect at an angle of essentially 90° and extend at an angle of essentially 45° both in relation to the X direction and in relation to the Y direction.

In a device according to the present invention, the transmitters 10, 10' and receivers 11, 11' of the light barriers 9, 9' are each preferably positioned in a tunnel 17. In this way, the interfering influence of the laboratory illumination and/or daylight is reduced. If a device 1 is mounted on each of the first and third places for accommodating a microplate on a carrier, the alignment of the carrier 16 may be accelerated even more. A plate 14 may also have four light barriers (not shown), which may be switched over in such a way that only two intersecting light barriers are active at a time. A system 4 for working with fluid-containing samples 5, which includes at least one device 1 just described, is preferred. Such a system 4 having a robot arm 7, which includes multiple seats 18 for functional elements 2, is especially preferred. Preferred functional elements are pipette and/or dispenser tips 20 in this case. These seats 18 include correction elements 19 which are implemented for exerting a force on each functional element 2 and therefore for correcting the position of each functional element 2 in its seat 18 in the X and/or Y and/or Z directions. In this case, these correction elements 19, 19' act on the functional elements 2 in a direction which corresponds either to the extension direction of the detection beam 12 of the first light barrier 9 or to the extension direction of the detection beam 12' of the second light barrier 9'. These correction elements 19, 19' are preferably implemented as screws or piezoelements. In this case, grub screws having a hexagon socket have especially proven themselves. Piezoelements have the advantage over the screws that the adjustment of the position of the corresponding functional element 2, i.e., a pipette tip, for example, maybe corrected automatically. In contrast, the higher production costs and shorter adjustment paths may be considered disadvantageous for piezoelements.

Figure 4:
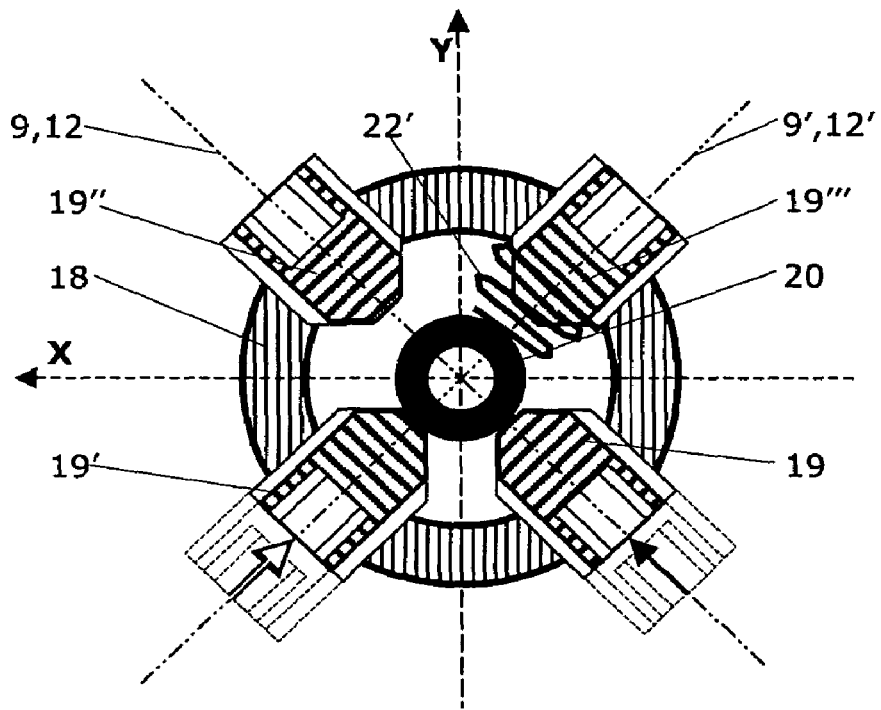
FIG. 4 shows a horizontal section through the seat of a functional element on the robot arm having the correction elements according to the present invention for aligning the functional element.

In a more complex embodiment, each seat 18 for functional element 2 includes four correction elements 19, 19', 19'', 19''', each two of which lie diametrically opposite the other two and supplement their effect. It is especially preferable if the adjustment direction of each of these correction elements 19, 19', 19'', 19''' corresponds precisely to an extension direction of the detection beam 12, 12' of a light barrier 9, 9' of the device 1 according to the present invention. It has been shown that in most cases, fixing the functional element 2 by tightening the screws or piezoelements 19'', 19''' diametrically opposing the adjusted correction elements 19, 19' may be dispensed with. However, it may be necessary sometimes, so that additional time must be used for this fixing. As a compromise solution, using which the fixing time may be saved, a seat 18, in which each correction element 19, 19' is assigned an opposing spring 22, 22' (cf. FIG. 4), is provided as a simpler embodiment.

A method for aligning pipette and/or dispenser tips 20 on the wells 23 of a standard microplate 15 positioned in the work field 6 of a system 4 is also suggested. All pipette and/or dispenser tips 20 to be aligned are moved in the X direction (cf. FIG. 3) or Y direction (not shown) through the two light barriers (9, 9'), the X and Y values (X1/Y1 and X2/Y2 in FIG. 3) of the corresponding pipette and/or dispenser tips 20 being detected and stored in the computer 13 upon each interruption of the detection beams 12, 12'. First and second correction values for each of the pipette and/or dispenser tips 20 to be aligned are calculated from the stored X and Y values. The pipette and/or dispenser tips 20 to be aligned are brought one after another into a correction position (black circular disk in FIG. 3). From this correction position, the pipette and/or dispenser tips 20 are adjusted by their individual correction values (white and/or black arrow in FIG. 3) via activation of the corresponding correction elements 19, 19' until the tips 20 assume their final position in the intersection point of the detection beams 12, 12' of the light barriers 9, 9' (dashed circle in FIG. 3).

If piezoelements are used as correction elements 19, 19', this method may be controlled by the computer 13 and run automatically. If simple grub screws are used as correction elements 19, 19', the adjustment procedure may be monitored using the computer and an acoustic signal may be triggered upon each interruption of the light barriers 9, 9', which indicates to the operator that the end of each individual correction value has been reached.

The device 1 may also be used for a check of the current position of pipette or dispenser tips 20. Before the execution of the liquid handling work, this is preferably performed by placing a plate 14 having the intersecting light barriers 9, 9' on a high-precision carrier 16. The position of the individual functional elements 2 placed in a robot arm and also the position of the carrier 16 are checked in a single operation and—if necessary—stored in a computer file. The printout of such a file may be attached to the pipette or dispenser log. The plate 14 is removed again before executing the liquid handling. The placement and removal of the plate 14 is preferably performed automatically by a further robot arm (not shown) or manually by an operator.

The current position of pipette or dispenser tips 20 may also be checked during the execution of the liquid handling tasks. For this purpose, a plate 14 having the intersecting light barriers 9, 9' is placed permanently at a predetermined position on a high-precision carrier 16. In this case, the current tip position may be checked at any time and/or sporadically. If a previously determined error value in the position is exceeded, a warning signal may be output, a corresponding log may be prepared, or the liquid handling procedure may even be stopped. If piezoelements 19, 19' are used, it is also possible to readjust the position of the tips 20 during the execution of a long-lasting liquid handling process.

What is claimed is:

1. A plate for use in positioning functional elements in a laboratory system for handling samples containing liquids, the laboratory system having a high-precision carrier for standard microplates and comprising a substantially horizontal work field having a lengthwise dimension in an X direction and a transverse dimension in a Y direction extending substantially perpendicularly to the length-wise dimension, and at least one robot arm having at least one functional element aligned substantially perpendicularly to the work field in a Z direction, the robot arm being able to move the functional element in at least a partial region of the work field in at least one of the X or Y or Z directions, the X, Y and Z directions defining a right-angle coordinate system for moving the robot arm or the functional element, respectively, the plate being positionable within the partial regions of the work field and comprising:

two light barriers having two respective detection beams which intersect inside the partial region of the work field;

each light barrier having a transmitter and a receiver;

the plate having external dimensions of a standard microplate and being fixable in a precise position on the high-precision carrier for the standard microplates positioned within the work field;

the light barriers being so arranged on the plate that the directions of emission of the two detection beams extend in a direction deviating from parallels to outer edges of the plate.

2. The plate according to claim 1, wherein the detection beams of the light barriers intersect at an angle of substantially 90° and extend at an angle of substantially 45° in relation to the outer edges of the plate.

3. The plate according to claim 1, wherein the transmitters and receivers of the light barriers are each positioned in a tunnel.

4. The plate according to claim 1, wherein the two light barriers are positioned on the plate, the detecting beams of the light barriers intersecting at a point, which is located in a defined position in relation to a well A1 of a standard microplate.

5. The plate according to claim 4, wherein the point of intersection of the detecting beams of the light barriers is located at a distance from the middle of the plate.

6. A laboratory system for the handling of samples containing liquids comprising a computer controlling a robot arm, wherein the laboratory system comprises at least one plate in accordance with claim 1, the computer detecting the movements of the robot arm or the functional element, respectively, and analyzing signals from the receivers.

7. The laboratory system according to claim 6, wherein the computer correlates these signals with an X, Y and Z direction position of the functional element in the work field, which triggers the signals.

8. The laboratory system according to claim 6, having a robot arm, which includes one single seat or multiple seats for functional elements, the seats including correction elements which exert a force on each functional element and therefore to correct the position of each functional element in its seat in at least one of the X, Y or Z directions, wherein the correction elements act on the functional elements in a direction which corresponds either to the extension direction of the detecting beam of the first light barrier or to the extension direction of the detecting beam of the second light barrier.

9. The laboratory system according to claim 8, wherein the functional elements are pipette or dispenser tips or as reference needles, which are raised and lowered in the Z direction.

10. The laboratory system according to claim 8, wherein the correction elements are screws or piezoelements.

11. The laboratory system according to claim 10, wherein each correction element is assigned an opposing spring.

12. The laboratory system according to claim 8, wherein each seat for a functional element includes four correction elements, two of which lie diametrically opposite the other two and supplement their effect.

13. A method for positioning containers on the work field of a laboratory system for working with fluid-containing samples, the laboratory system including an substantially horizontal work field having a lengthwise X direction and a transverse dimension Y direction extending substantially perpendicularly thereto, as well as at least one robot arm having at least one functional element aligned substantially perpendicularly to the work field in a Z direction, the functional element being moved in at least a partial region of the work field at least in one of the X or Y or Z directions using the robot arm, the X, Y and Z directions defining a right-angle coordinate system for moving the robot arm or the functional element, respectively, method comprising:

positioning two intersecting light barriers on a plate and within a partial region of the work field, the light barriers each having a transmitter and a receiver;

the plate having the external dimensions of a standard microplate and being fixed in a first precise position on a high-precision carrier for standard microplates positioned within the work field;

the light barriers being so arranged on the plate that the directions of emission of the two detection beams extend in a direction deviating from parallels to the outer edges of the plate.

14. The method according to claim 13, wherein the detection beams of the light barriers intersect at an angle of substantially 90° and extend at an angle of substantially 45° both in relation to the outer edges of the plate.

15. The method according to claim 13, wherein movements of the robot arm or of the functional element, respectively, are detected using a computer, which analyses the signals of the receivers and correlates these signals with an X/Y position of the functional element (2) in the work field, which triggers the signals.

16. The method according to claim 13, wherein by using the robot arm, a reference needle is positioned in the intersection point of the detection beams of the light barriers, and the X, Y and Z values of this first reference point are stored in the computer.

17. The method according to claim 16, wherein the plate is fixed in a second position on the same high-precision carrier for standard microplates, the robot arm having the reference needle being positioned in a theoretical intersection point of the detection beams of the light barriers, and moving the high-precision carrier in the X or Z directions until the reference needle is located in the intersection point of the detection beams of the light barriers.

18. A method for aligning pipette or dispenser tips on the wells of a standard microplate positioned in the working field of a laboratory system wherein the container is aligned by the procedure according to claim 17, and wherein all pipette or dispenser tips to be aligned are moved in the X or Y direction through the two light barriers, X and Y values of the corresponding pipette or dispenser tips being detected and stored in the computer upon each interruption of the detection beams.

19. The method according to claim 18, wherein first and second correction values for each of the pipette or dispenser tips to be aligned are calculated from the stored X and Y values and the pipette or dispenser tips to be aligned are brought into a correction position one after another, from which the pipette or dispenser tips are adjusted by using activation of the corresponding correction elements, the pipette or dispenser tips being dis-placed by their individual correction values until they assume their final position in the intersection point of the detection beams of the light barriers.

20. The method according to claim 13, being controlled by the computer and running automatically.

21. The method according to claim 18, being controlled by the computer and running automatically.

* * * * *